United States Patent
Hassett et al.

(10) Patent No.: US 8,052,680 B2
(45) Date of Patent: Nov. 8, 2011

(54) PROCESS AND DEVICE FOR THE TREATMENT OF ATRIAL ARRHYTHMIA

(75) Inventors: James A. Hassett, Bloomington, MN (US); John F. Swartz, Afton, OK (US); Michael C. Bednarek, Buffalo, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1297 days.

(21) Appl. No.: 11/545,943

(22) Filed: Oct. 10, 2006

(65) Prior Publication Data

US 2007/0032787 A1 Feb. 8, 2007

Related U.S. Application Data

(60) Division of application No. 10/401,798, filed on Mar. 31, 2003, now Pat. No. 7,118,568, which is a division of application No. 09/814,890, filed on Mar. 22, 2001, now Pat. No. 6,540,744, which is a division of application No. 09/233,337, filed on Jan. 20, 1999, now Pat. No. 6,251,109, which is a continuation-in-part of application No. 08/883,668, filed on Jun. 27, 1997, now Pat. No. 5,938,660.

(51) Int. Cl.
*A61B 18/04* (2006.01)
*A61B 18/14* (2006.01)

(52) U.S. Cl. ............... 606/45; 606/27; 606/41; 606/50

(58) Field of Classification Search .................. 606/41, 606/45, 46, 49, 50, 27; 607/101, 102, 122
See application file for complete search history.

(56) References Cited

U.S. PATENT DOCUMENTS 3,867,945 A 2/1975 Long
(Continued)

FOREIGN PATENT DOCUMENTS

DE 4001086 7/1991
(Continued)

OTHER PUBLICATIONS

Cox, J.J.L.et al., Electrophysiology, Pacing and Arrhythmia, "Operations for Atrial Fibrillation," Clin. Cardiol., vol. 14, pp. 827-834 (1991).

(Continued)

*Primary Examiner* — Roy D Gibson
(74) *Attorney, Agent, or Firm* — Wiley Rein LLP (57) ABSTRACT

A process for preventing atrial premature contractions originating within a pulmonary vein from being conducted into the left atrium of a human heart. More specifically, an ablation lesion is formed which electrically isolates the located source of the atrial premature contraction in the pulmonary vein from connection with the left atrium and blocks passage of the atrial premature contraction originating from the located source. In one embodiment, the steps of the process include advancing a medical device into the left atrium of a human heart, introducing the advanced medical device into the pulmonary vein from the left atrium of a human heart, sensing electrical activity within the pulmonary vein using the introduced medical device, locating a source of the atrial premature contraction within the pulmonary vein using the sensed electrical activity, and forming an ablation lesion in tissue of the pulmonary vein at a location proximal from the located source of the atrial premature contraction within the pulmonary vein. Conductive media and various medical devices may be used with the process.

20 Claims, 10 Drawing Sheets

U.S. PATENT DOCUMENTS

| | | |
|---|---|---|
| 4,033,331 A | 7/1977 | Guss et al. |
| 4,117,836 A | 10/1978 | Erikson |
| 4,244,362 A | 1/1981 | Anderson |
| 4,445,892 A | 5/1984 | Hussein et al. |
| 4,500,529 A | 2/1985 | Shanklin, Jr. et al. |
| 4,558,155 A | 12/1985 | Shanklin, Jr. et al. |
| 4,569,347 A | 2/1986 | Frisbie |
| 4,581,017 A | 4/1986 | Sahota |
| 4,641,649 A | 2/1987 | Wilinsky et al. |
| 4,705,517 A | 11/1987 | DiPisa, Jr. |
| 4,721,117 A | 1/1988 | Mar et al. |
| 4,729,384 A | 3/1988 | Bazenet |
| 4,790,331 A | 12/1988 | Okada et al. |
| 4,810,244 A | 3/1989 | Allen |
| 4,838,879 A | 6/1989 | Tanabe et al. |
| 4,867,174 A | 9/1989 | Skribiski |
| 4,882,777 A | 11/1989 | Narula |
| 4,883,058 A | 11/1989 | Ruiz |
| 4,898,591 A | 2/1990 | Jang et al. |
| 4,911,163 A | 3/1990 | Fina |
| 4,917,102 A | 4/1990 | Miller et al. |
| 4,935,017 A | 6/1990 | Sylvanowicz |
| 4,945,912 A | 8/1990 | Langberg |
| 4,955,377 A | 9/1990 | Lennox et al. |
| 4,969,875 A | 11/1990 | Ichikawa |
| 4,988,698 A | 1/1991 | Kato et al. |
| 5,002,532 A | 3/1991 | Gaiser et al. |
| 5,016,640 A | 5/1991 | Ruiz |
| 5,100,388 A | 3/1992 | Behl et al. |
| 5,103,804 A | 4/1992 | Abele et al. |
| 5,106,360 A | 4/1992 | Ishiwara et al. |
| 5,120,323 A | 6/1992 | Shockey et al. |
| 5,147,315 A | 9/1992 | Weber |
| 5,162,911 A | 11/1992 | Burrage |
| 5,171,232 A | 12/1992 | Castillo et al. |
| 5,172,699 A | 12/1992 | Svenson et al. |
| 5,209,229 A | 5/1993 | Gilli |
| 5,215,540 A | 6/1993 | Anderhub |
| 5,215,989 A | 6/1993 | Baldwin et al. |
| 5,222,501 A | 6/1993 | Iddeker et al. |
| 5,228,442 A | 7/1993 | Imran |
| 5,231,994 A | 8/1993 | Harmjanz |
| 5,231,995 A | 8/1993 | Desai |
| 5,242,441 A | 9/1993 | Avitall |
| 5,246,007 A | 9/1993 | Frisbie et al. |
| 5,246,438 A | 9/1993 | Langberg |
| 5,256,141 A | 10/1993 | Gencheff et al. |
| 5,263,493 A | 11/1993 | Avitall |
| 5,267,982 A | 12/1993 | Sylvanowicz |
| 5,271,392 A | 12/1993 | Ferek-Petric |
| 5,279,546 A | 1/1994 | Mische et al. |
| 5,281,213 A | 1/1994 | Milder et al. |
| 5,281,217 A | 1/1994 | Edwards et al. |
| 5,281,218 A | 1/1994 | Imran |
| 5,282,836 A | 2/1994 | Kreyenhagen et al. |
| 5,286,866 A | 2/1994 | Carr et al. |
| 5,287,858 A | 2/1994 | Hammerslag et al. |
| 5,290,229 A | 3/1994 | Paskar |
| 5,293,868 A | 3/1994 | Nardella |
| 5,295,493 A | 3/1994 | Radisch, Jr. |
| 5,299,574 A | 4/1994 | Bower |
| 5,304,131 A | 4/1994 | Paskar |
| 5,304,214 A | 4/1994 | DeFord et al. |
| 5,312,355 A | 5/1994 | Lee |
| 5,322,509 A | 6/1994 | Richerd |
| 5,366,490 A | 11/1994 | Edwards et al. |
| 5,427,119 A | 6/1995 | Swartz et al. |
| 5,433,729 A | 7/1995 | Adams et al. |
| 5,450,846 A | 9/1995 | Goldreyer |
| 5,462,529 A | 10/1995 | Simpson et al. |
| 5,468,239 A | 11/1995 | Tanner et al. |
| 5,472,441 A | 12/1995 | Edwards et al. |
| 5,476,495 A | 12/1995 | Kordis et al. |
| 5,482,037 A | 1/1996 | Borghi |
| 5,484,412 A | 1/1996 | Pierpont |
| 5,497,774 A | 3/1996 | Swartz et al. |
| 5,500,012 A | 3/1996 | Brucker et al. |
| 5,536,247 A | 7/1996 | Thornton |
| 5,540,679 A | 7/1996 | Fram et al. |
| 5,564,440 A | 10/1996 | Swartz et al. |
| 5,575,766 A | 11/1996 | Swartz et al. |
| 5,584,872 A | 12/1996 | LaFontaine et al. |
| 5,588,961 A | 12/1996 | Leone et al. |
| 5,599,307 A | 2/1997 | Bacher et al. |
| 5,624,439 A | 4/1997 | Edwards et al. |
| 5,628,316 A | 5/1997 | Swartz et al. |
| 5,640,955 A | 6/1997 | Ockuly et al. |
| 5,676,693 A | 10/1997 | LaFontaine |
| 5,681,308 A | 10/1997 | Edwards et al. |
| 5,722,400 A | 3/1998 | Ockuly et al. |
| 5,746,495 A | 5/1998 | Klamm |
| 5,785,706 A | 7/1998 | Bednarek |
| 5,792,105 A | 8/1998 | Lin et al. |
| 5,797,905 A | 8/1998 | Fleischman et al. |
| 5,800,482 A | 9/1998 | Pomeranz et al. |
| 5,807,306 A | 9/1998 | Shapland et al. |
| 5,814,029 A | 9/1998 | Hassett |
| 5,938,660 A | 8/1999 | Swartz et al. |
| 5,971,983 A | 10/1999 | Lesh |
| 6,068,629 A | 5/2000 | Haissaguerre et al. |
| 6,097,976 A | 8/2000 | Yang et al. |
| 6,120,500 A | 9/2000 | Bednarek et al. |
| 6,156,018 A | 12/2000 | Hassett |
| 6,179,824 B1 | 1/2001 | Eggers et al. |
| 6,217,576 B1 | 4/2001 | Tu et al. |
| 6,235,025 B1 | 5/2001 | Swartz et al. |
| 6,251,109 B1 | 6/2001 | Hassett et al. |
| 6,503,247 B2 | 1/2003 | Swartz et al. |
| 6,526,302 B2 | 2/2003 | Hassett |
| 6,540,744 B2 | 4/2003 | Hassett et al. |

FOREIGN PATENT DOCUMENTS

| | | |
|---|---|---|
| EP | A 656217 | 6/1995 |
| EP | A 670168 | 9/1995 |
| WO | WO 92/12754 | 8/1992 |
| WO | WO 92/19307 | 11/1992 |
| WO | WO 96/00042 | 1/1996 |
| WO | WO 97/16127 | 5/1997 |

OTHER PUBLICATIONS

Cox, J.J.L. et al., "The Surgical Treatment of Atrial Fibrillation," The Journal of Thoracic and Cardiovascular Surgery, vol. 101, No. 4, pp. 569-592 (Apr. 1991).

Cox, J.J.L. et al., "The Surgical Treatment of Atrial Fibrillation," The Journal of Thoracic and Cardiovascular Surgery, vol. 101, No. 4, pp. 406-426 (Mar. 1991).

Falk, R.H. et al., Atrial Fibrillation Mechanisms and Management, p. 359-374 (1992).

Horowitz, L.N., Current Management of Arrhythmias, pp. 373-378 (1991).

Martin, D. et al., "Atrial Fibrillation," pp. 35-41 (1994).

Martin, D. et al., "Atrial Fibrillation," pp. 42-59 (1994).

Martin, D. "Atrial Fibrillation," pp. 52-59 (1994).

Singer, I., et al., "Catheter Ablation for Arrhythmias," Clinical Manual of Electrophysiology, pp. 421-431 (1993).

Haissaguerre, M. et al., "Right and Left Atrial Radiofrequency Catheter Therapy of Paroxysmal Atrial Fibrillation," Journal of Cardiovascular Electrophysiology, vol. 7, No. 12, pp. 1132-1144 (Dec. 1996).

Heinz, G. et al., "Improvement of Left Ventricular Systolic Function After Successful Radiofrequency His Bundle Ablation for Drug Refractory, Chronic Atrial Fibrillation and Recurrent Atrial Flutter," Am. J. Cardiol. vol. 69, pp. 489-492 (1992).

Huang, S.K. et al., "Closed Chest Catheter Desiccation of the Atrioventricular Junction Using Radiofrequency Energy—A New Method of Catheter Ablation," J. Am. Coll. Cardiol., vol. 9, pp. 349-358 (1987).

Gallagher, J.J. et al., "Catheter Technique for Closed-Chest Ablation of the Atrioventricular Conduction System," N. Engl. J. Med., vol. 306, pp. 1994-200 (1982).

Saul, J.P. et al., "Catheter Ablation of Accessory Atrioventricular Pathways in Young Patients: Use of Long Vascular Sheaths, the Transseptal Approach and a Retrograde Left Posterior Parallel Approach," J. Amer. Coll. Card., Vol. 21, No. 3, pp. 571-583 (Mar. 1, 1993).

Scheinman, M.M. et al., "Catheter-Induced Ablation of the Atrial Ventricular Juncture to Control Refractory Supraventricular Arrhythmias," JAMA, vol. 248, pp. 851-855 (1982).

Swartz, J.F. et al., "Radiofrquency Endocardial Catheter Ablation of Accessory Atrioventricular Pathway Atrial Insertion Sites," Circulation, vol. 87, No. 2, pp. 487-499 (Feb. 1993).

Tracey, C.N., "Radiofrequency Catheter Ablation of Ectopic Atrial Tachycardia Using Paced Activation Sequence Mapping," J. Am. Coll. Cardiol., vol. 21, pp. 910-917 (1993).

PROCESS AND DEVICE FOR THE TREATMENT OF ATRIAL ARRHYTHMIA

CROSS-REFERENCE TO RELATED APPLICATIONS

This application is a divisional of U.S. application Ser. No. 10/401,798, filed 31 Mar. 2003 (the '798 application), now U.S. Pat. No. 7,118,568, which is a divisional of U.S. application Ser. No. 09/814,890, filed 22 Mar. 2001, now U.S. Pat. No. 6,540,744 (the '744 patent), which is a divisional of U.S. application Ser. No. 09/233,337, filed 20 Jan. 1999, now U.S. Pat. No. 6,251,109 (the '109 patent), which is a continuation-in-part of U.S. application Ser. No. 08/883,668, filed 27 Jun. 1997, now U.S. Pat. No. 5,938,660 (the '660 patent). The '798 application, the '744 patent, the '109 patent, and the '660 patent are all hereby incorporated by reference as though fully set forth herein.

BACKGROUND OF THE INVENTION a. Field of the Invention

This invention relates to medical devices and processes useful for the treatment of atrial arrhythmia. In particular, it relates to a preferred process and medical device used for ablation procedures in vessels of the human body, namely the pulmonary veins.

b. Background Art

Introducers and catheters have been in use for medical procedures for many years. For example, one procedure utilizes a catheter to convey an electrical stimulus to a selected location within the human body. Another procedure utilizes a catheter to monitor activity in various locations in the body for diagnostic tests. Thus, catheters may examine, diagnose and treat while positioned at specific locations within the body which are otherwise inaccessible without more invasive procedures. In use, catheters may be inserted into a major vein or artery which is near the body surface. These catheters are then guided to a specific location for examination, diagnosis and treatment by manipulating the catheter through the artery or vein of the human body, frequently with the assistance of other medical devices, such as introducers or guidewires.

One common medical procedure utilizing specialized catheters is the treatment of vessels located within the human body, frequently vessels associated with the human heart. Those procedures, most notably angioplasty procedures, utilize a catheter which often contains an inflatable balloon secured to the catheter. In some of these medical procedures, the catheter contains a pair of inflatable balloons used to limit the portion of the vessel that is treated or to assure that the catheter remains at a fixed location within the vessel throughout the medical procedure or to assist in the performance of the medical procedure.

Multiple balloon catheters are utilized throughout the body. For example, U.S. Pat. No. 5,468,239 discloses a device for circumferential laser burning of tissue in a urethral canal. This device utilizes a pair of cuffs or balloons 60 with a laser probe 12 located between those balloons. U.S. Pat. No. 5,588,961 discloses an infusion catheter for delivery of medication to a vessel and contains a pair of balloons 16, 17 and an electrode 35 secured to the catheter. Ports are provided in the catheter to introduce the medication into the space between the two balloons within the vessel. Energy may also be introduced into the electrode to encourage the movement of the medication away from the catheter toward the walls of the vessel. U.S. Pat. No. 5,256,141 discloses a pair of balloons (14, 18) with an electrode secured to a catheter to apply a controlled electric charge to material introduced into the space in the vessel between the two balloons.

Biological material may also be introduced into this space for medical treatment of the vessel. U.S. Pat. No. 5,366,490 discloses a pair of balloons 30, 32 secured to a catheter and a stylette 36. Radio frequency energy is supplied to the catheter to destroy tissue. U.S. Pat. No. 5,599,307 discloses a pair of balloons 41, 42 secured to a catheter designed to occlude a vessel. U.S. Pat. No. 5,002,532 discloses a pair of balloons 21, 22 secured to a catheter 12 for use in a dilation procedure within a vessel, whereby the two balloons may be inflated to different extents. U.S. Pat. No. 5,792,105 discloses a multi-channel balloon catheter for delivering fluids which utilizes an inner and an outer balloons. See also U.S. Pat. No. 4,445,892.

In addition to the use of multiple balloons on a single catheter for medical procedures, U.S. Pat. No. 5,462,529 discloses a medical device containing a pair of catheters 12, 28, each containing a balloon 20, 48 secured at or near its distal end, which device is utilized to perform a medical procedure within a vessel. U.S. Pat. No. 5,484,412 also discloses a pair of catheters 18, 22 utilized to perform a medical procedure within a vessel, each containing an inflatable balloon 36, 38. U.S. Pat. No. 4,911,163 discloses a pair of balloons (2, 8) secured to a pair of catheters 1, 7 for introduction of medicine or diagnostic fluids into the space between the two balloons.

Atrial fibrillation is the most common sustained heart arrhythmia. It is estimated to occur in upwards of 0.4 percent of the adult population and perhaps as many as 10 percent of the population who are 60 years or older. Cox, J. L., et al., Electrophysiology, Pacing and Arrhythmia, "Operations for Atrial Fibrillation," Clin. Cardiol. 14, 827-834 (1991).

Atrial arrhythmia may be transient or persistent. While most atrial arrhythmia occur in individuals having other forms of underlying heart disease, some atrial arrhythmia occur independently. While atrial arrhythmia do not directly cause death as frequently as ventricular arrhythmia, they increase the risk factors for a number of other diseases such as systemic and cerebral embolism and may cause a number of additional medical problems.

In the treatment of atrial arrhythmia, antiarrhythmic drugs sometimes provide relief. Other treatments for atrial arrhythmia or fibrillation involve the use of an implanted atrial defibrillator or cardioversion. See, for example, U.S. Pat. Nos. 5,282,836, 5,271,392 and 5,209,229 and Martin, D., et al., Atrial Fibrillation, pgs. 42-59 (1994).

Certain patients with symptomatic or life threatening atrial arrhythmia, however, cannot be adequately treated by drugs or these types of medical devices. Other forms of aggressive treatment are sometimes mandated, which have in the past included surgery. For example, a surgical procedure for the treatment of atrial arrhythmia known as the "Maze" procedure is discussed in Cox, J. L. et al., Electrophysiology, Pacing and Arrhythmia, "Operations for Atrial Fibrillation," Clin. Cardiol. Vol. 14, pgs. 827-834 (1991).

Another procedure increasingly used within the last 10 to 15 years for the treatment of certain types of cardiac arrhythmia involves ablation of cardiac tissue. For example, this procedure has been commonly used to interrupt or modify existing conduction pathways associated with arrhythmia within the heart. The particular area for ablation depends on the type of underlying arrhythmia. The use of radio frequency catheter ablation for the treatment of paroxysmal atrial fibrillation is disclosed in Haissaguerre, M., et al., "Right and Left Atrial Radiofrequency Catheter Therapy of Paroxysmal Atrial Fibrillation" J. Cardiovascular Electrophsiology, V.7, pgs. 1132-1144 (December 1996). Ablation procedures have also been used for the treatment of atrioventricular (AV) nodal reentrant tachycardia. With this condition, ablation of the fast or slow AV nodal pathways has become an accepted treatment. Singer, I., et al., "Catheter Ablation for Arrhythmias" Clinical Manual of Electrophsiology, pgs. 421431 (1993); Falk, R. H., et al., Atrial Fibrillation Mechanisms in Management, pgs. 359-374 (1992); Horowitz, L. N., Current Management of Arrhythmias, pgs. 373-378 (1991); and Martin, D., et al., Atrial Fibrillation, pgs. 42-59 (1994). In addition, the use of ablation catheters for ablating locations within the heart has been disclosed, for example in U.S. Pat. Nos. 4,641,649, 5,263,493, 5,231,995, 5,228,442 and 5,281,217.

The sources of energy used for catheter ablation vary. Initially, high voltage, direct current (DC) ablation techniques were commonly used. However, because of problems associated with the use of DC current, radio frequency (RF) energy has become the preferred source of energy for ablation procedures. The use of RF energy for ablation has been disclosed, for example, in U.S. Pat. Nos. 4,945,912, 5,209,229, 5,281,218, 5,242,441, 5,246,438, 5,281,213 and 5,293,868. Other energy sources which are being used currently or are being considered for ablation of heart tissue include laser, ultrasound, microwave and fulgutronization.

Ablation of a precise location within the heart requires the precise placement of the ablation catheter within the heart. Precise positioning of the ablation catheter is especially difficult because of the physiology of the heart, particularly as the ablation procedures generally occur while the heart is beating. Commonly, the placement of the catheter is determined by a combination of electrophysiological guidance and fluoroscopy (placement of the catheter in relation to known features of the heart which are marked by radiopaque diagnostic catheters which are placed in or at known anatomical structures such as the coronary sinus, high right atrium and the right ventricle).

A process for the mapping and treatment of atrial arrhythmia using ablation catheters guided to a specific location by shaped, guiding introducers is disclosed in U.S. Pat. Nos. 5,427,119, 5,497,774, 5,575,766, 5,564,440, 5,628,316 and 5,640,955. In particular, a process for the ablation of defined tracks within the left and/or right atrium as an element of the treatment of atrial fibrillation is disclosed in U.S. Pat. No. 5,575,766.

The mechanism for initiation of some forms of atrial arrhythmia, such as atrial premature contractions, is not well understood. As a result, ablation procedures in the heart have focused on the formation of lesions within the chambers of the heart at selected locations which either prevent the passage of electrical signals associated with atrial premature contractions or prevent the formation of improper electrical pathways within the heart, which can result in atrial arrhythmia.

It has been surprisingly discovered that one source for these atrial premature contractions originates within vessels associated with the heart, in particular the pulmonary veins. Once these atrial premature contractions form in the pulmonary veins, they are periodically conducted into the left atrium. When the atrial premature contractions enter the left atrium, they can initiate or continue an episode of atrial fibrillation.

Invasive treatment of atrial fibrillation in the past around the pulmonary veins has been limited to the formation of lesions in the left atrium created by an invasive surgical procedure, such as is disclosed by Cox, J. L., et al., Electrophysiology, Pacing and Arrhythmia, "Operations for Atrial Fibrillation" Clin. Cardiol. Vol. 14, pgs. 827834 (1991). In addition, the use of precurved guiding introducers to guide ablation catheters to appropriate locations in the left atrium for use in the formation of lesions around the pulmonary veins has been disclosed in U.S. Pat. No. 5,575,766.

While these procedures have been successful in some patients, other patients require additional treatment as the treatments previously disclosed have not been completely successful in the elimination of the atrial fibrillation. In addition, these ablation procedures can be very time consuming, requiring as long as 10-15 hours.

It is therefore an aspect of this invention to disclose a medical device useful in the treatment of atrial arrhythmia, particularly atrial fibrillation.

It is an additional aspect of this invention to disclose a medical device useful for the formation of ablation lesions in vessels in the body.

It is a still further aspect of this invention to disclose a medical device containing a pair of inflatable balloons. one located inside of the other, and an ablation electrode, which components are utilized to form a circumferential ablation lesion for the treatment of atrial arrhythmia, particularly atrial premature contractions.

It is a still further aspect of this invention to disclose a process for the formation of circumferential ablation lesions in vessels in the human body.

It is a still further aspect of this invention to disclose a process for ablation of tissue located within the pulmonary veins, or on the os of the pulmonary veins.

It is a still further aspect of this invention to disclose a process for the formation of circumferential lesions in the pulmonary veins, or on the os of the pulmonary veins.

It is a still further aspect of this invention to disclose medical procedures for the production of circumferential ablation lesions within vessels of the heart, or on the os of those vessels, for the treatment of atrial fibrillation.

It is a still further aspect of this invention to disclose a process for the formation of ablation lesions within a vessel of the heart, or on the os of that vessel, using RF energy.

These and other aspects of the invention are disclosed by the processes for the treatment of atrial arrhythmia and the design of the medical products for use with those processes.

BRIEF SUMMARY OF THE INVENTION

The present invention is an ablation catheter useful for ablation procedures within a vessel of a human, or on the os of that vessel, particularly a pulmonary vein. A first and a second balloon are secured to the catheter, with the second balloon secured to the catheter and located inside the first balloon. The balloons, when inflated, seal the vessel and prevent substantially the flow of blood through the vessel around these balloons. An introduction system is also included as an element of the ablation catheter to introduce a conductive media to the space within the first and second balloons when inflated. The first balloon contains a plurality of balloon openings in its outside surface through which the conductive media is expelled to contact the tissue of the vessel. An ablating system is also included as an element of the ablation catheter, which system is secured to the catheter at a location within the first, outer balloon, but outside of the second, inner balloon. The ablating system includes one or more RF energy ablation electrodes, which may be in the form of a coil electrode or a ring electrode. The conductive media conducts the ablating energy from the ablating system out through the balloon openings in that first balloon to contact the tissue located in the vessel, or on the os of the vessel, adjacent to the balloon openings to form a circumferential ablation lesion in the vessel or on the os of the vessel.

Alternatively, the present invention is a medical device for ablation within a vessel of a human, or on the os of that vessel, and includes the catheter system discussed above used in conjunction with a shaped guiding introducer with a proximal and distal end and a lumen passing from its proximal to its distal end. The shaped introducer guides the ablation catheter to the desired location in the vessel, or on the os of that vessel, to perform the ablation procedure.

Also disclosed is a process for the ablation of tissue within a vessel of a human, particularly a pulmonary vein, which includes introducing an ablation catheter containing a first, and a second balloon and an electrode into the vessel, or on the os of the vessel, wherein the second balloon is located within the first balloon, sealing the vessel to prevent substantially the flow of blood through the vessel using the first and second balloons, passing conductive media from within the first balloon through a plurality of balloon openings in the surface of the first balloon and conducting energy from the ablation electrode by use of the conductive media to contact the tissue within the vessel, or the os of the vessels, resulting in the formation of a circumferential ablation lesion.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
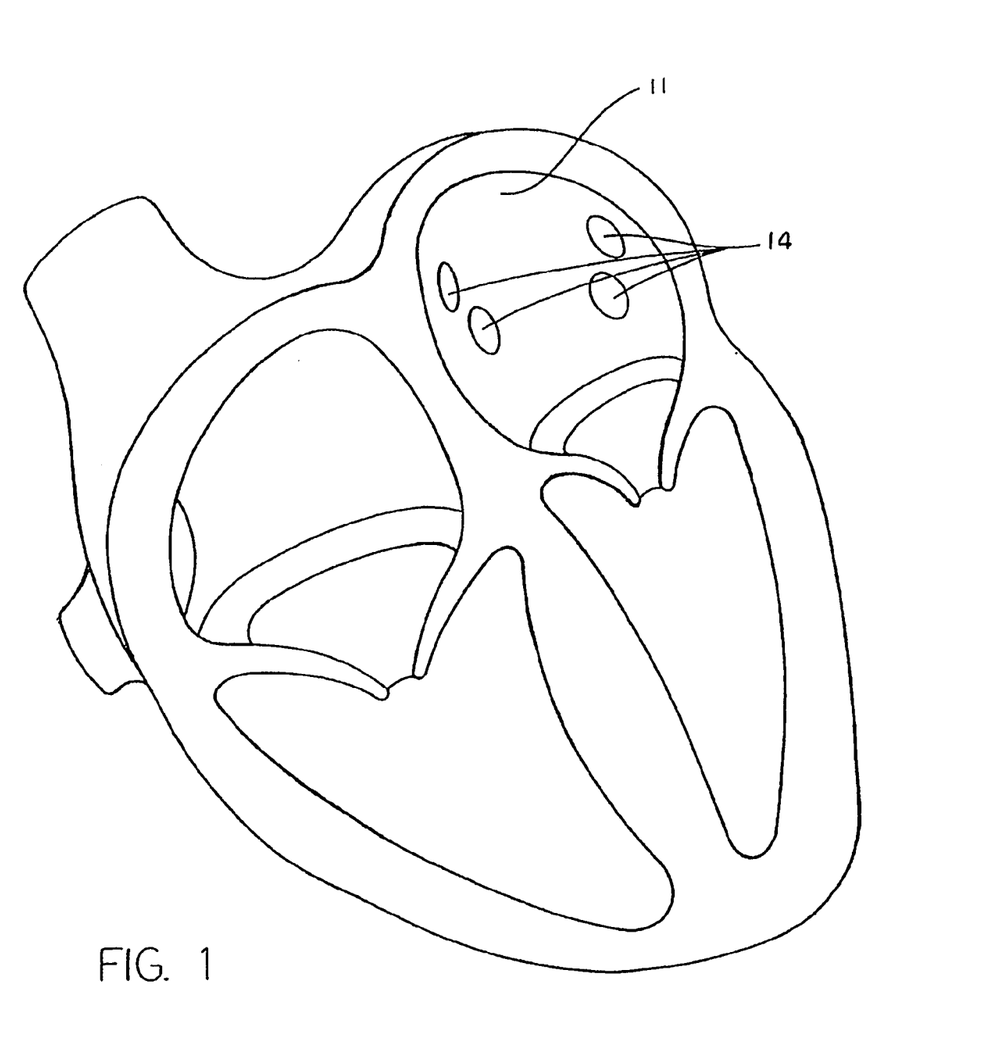
FIG. 1 is a cut away view of the heart showing the left atrium and the four pulmonary veins.

A typical human heart includes a right ventricle, a right atrium, a left ventricle and a left atrium. The right atrium is in fluid communication with the superior vena cava and the inferior vena cava. The atrioventricular septum separates the right atrium from the right ventricle. The tricuspid valve contained within the atrioventricular septum provides communication between the right atrium and the right ventricle. On the inner wall of the right atrium where it is connected with the left atrium is a thin walled, recessed portion, the fossa ovalis. A drawing of a human heart with the left atrium 11 and the openings os into the respective pulmonary veins 14 is shown in FIG. 1.

In a normal heart, contraction and relaxation of the heart muscle (myocardium) takes place in an organized fashion as electro-chemical signals pass sequentially through the myocardium from the sinoatrial (SA) node to the atrioventricular (AV) node and then along a well defined route which includes the His-Purkinje system into the left and right ventricles. Initial electrical impulses are generated at the SA node and conducted to the AV node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the atria which are referred to as atrial arrhythmia. Three of the most common arrhythmia are ectopic atrial tachycardia, atrial fibrillation and atrial flutter. Atrial fibrillation can result in significant patient discomfort and even death because of a number of associated problems, including: (1) an irregular heart-rate which causes the patient discomfort and anxiety, (2) loss of synchronous, atrioventricular contractions which compromises cardiac hemodynamics resulting in varying levels of congestive heart failure, and (3) stasis of blood flow, which increases the-vulnerability of the patient to thromboembolism.

Efforts to alleviate these problems have included significant usage of pharmacological treatments and occasionally surgical procedures. It has been discovered that similar success can be achieved without invasive surgery by ablation procedures performed within the atria as disclosed in U.S. Pat. No. 5,575,766. To accomplish this non-invasive procedure successfully, the ablation catheter must be positioned at pre-determined locations within the right and left atria to ablate predetermined tracks, thus forming a natural barrier to the formation of reentry circuits.

The specific pathological cause for atrial fibrillation is not well understood. It has been surprisingly discovered that one source for atrial premature contractions which may cause atrial fibrillation, particularly paroxysmal atrial fibrillation, originates in the pulmonary veins associated with the left atrium of the heart.

Figure 2:
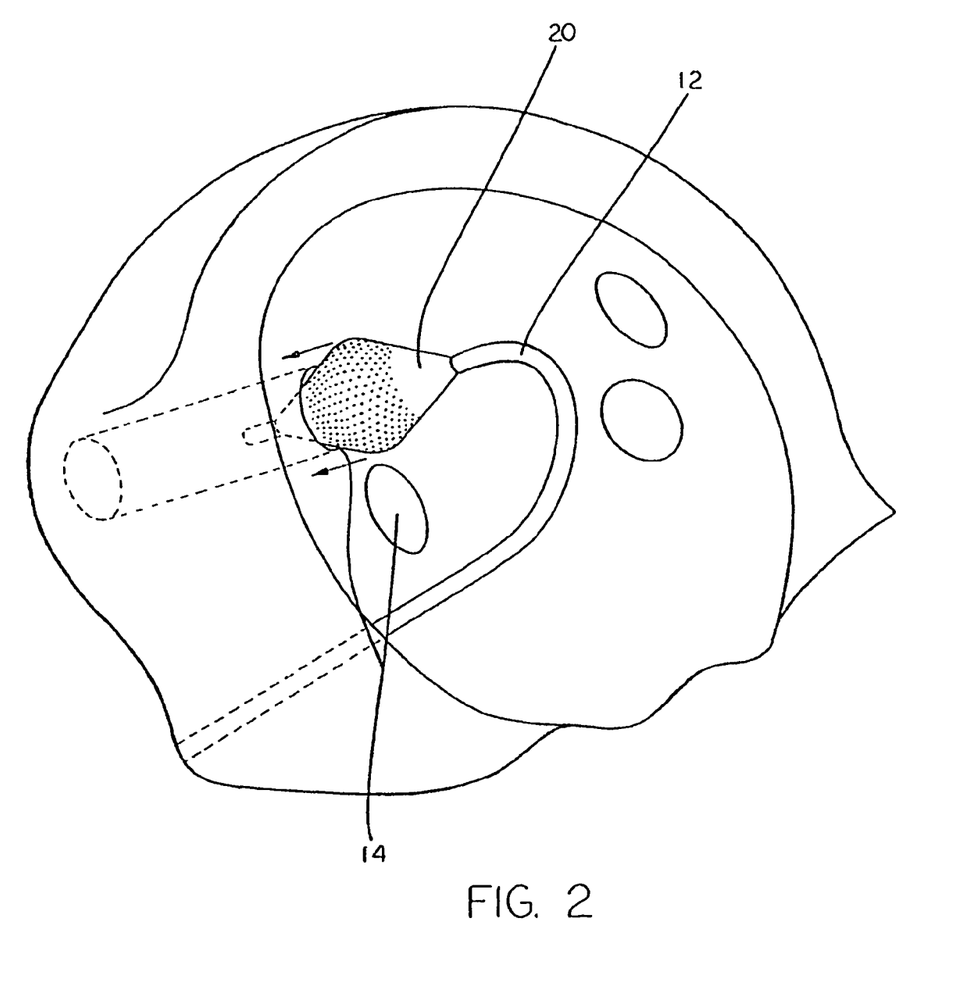
FIG. 2 is a cut away view of the left atrium showing the ablation catheter of the present invention being introduced into one of the pulmonary veins.
Figure 2A:
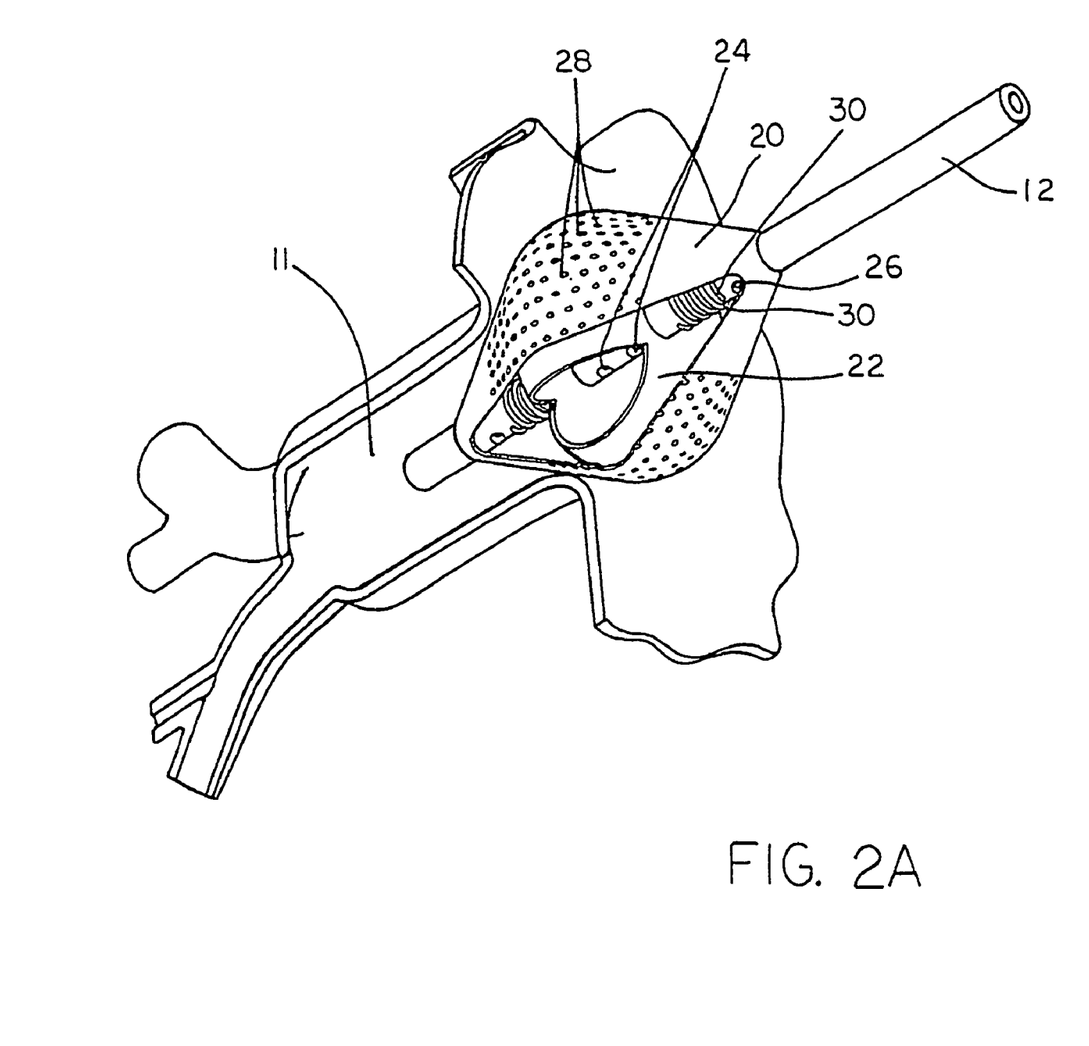
FIG. 2A is a cut away view of the ablation catheter of the present invention being introduced into one of the pulmonary veins.

In order to understand the structure of the medical devices of the invention, the medical procedure for their use within the heart must first be understood. In use, the medical device 10 of the present invention is advanced into the left atrium 11 and is then introduced into the appropriate pulmonary vein 14 or os of that pulmonary vein as shown in FIGS. 2 and 2A. (It is understood that ablation procedures may be necessary in more than one of the pulmonary veins. However, for purposes of discussion of the invention, the process will be limited to medical procedures performed in a single pulmonary vein) once in place, the ablation catheter 12 creates a lesion which electrically isolates the source of the atrial premature contraction in the pulmonary vein 14 from connection with the left atrium 11.

The pulmonary veins 14 are generally tubular in structure, increasing in size as they open into the left atrium 11. It has been discovered that the conduction of atrial premature contraction through a pulmonary vein 14 into the left atrium 11 can be completely halted by formation of a circumferential ablation lesion around the pulmonary vein 14, or in some circumstances around the os of the pulmonary vein, at a location proximal from the source of the atrial premature contraction. Merely ablating a single point on the surface of the pulmonary vein (14), which is perceived to be the source of the premature atrial contraction, may not be sufficient to isolate the source of the atrial premature contraction from the left atrium 11.

It is also important that the medical practitioner be able to monitor the electrical activity of the pulmonary vein 14 both before and after the ablation procedure is complete to assure that the source of atrial premature contraction has been successfully isolated from the left atrium 11.

Conventional procedures for ablation within the heart generally utilize either a conventional tip electrode or one or more ring electrodes on an ablation catheter. To effectively and efficiently ablate tissue, these electrodes are relatively small in diameter, usually in the range of about 5 French to about 8 French (1 French equals one-third millimeter (0.039 in.)). Because the diameter of a pulmonary vein 14 may be as large as about 20 millimeters (0.79 in.), it is impractical to use a conventional ablation electrode on a conventional ablation catheter to form the circumferential lesion around the inside of a pulmonary vein 14.

The steps of the process in one embodiment of the present invention for the formation of a circumferential ablation lesion within a pulmonary vein 14 include introducing into a pulmonary vein 14, or into the os of the pulmonary vein, an ablation catheter: 12 containing a pair of balloons 20, 22, one located within the other, to prevent the flow of blood through the pulmonary vein 14 as shown in FIGS. 2 and 2A. The ablation catheter 12 also includes an ablating system for ablating tissue, which system is secured to the catheter 12 but located inside the pair of balloons 20, 22. Finally the tissue within the pulmonary vein 14, or the os of the pulmonary vein, is ablated at a location proximal to the source of the atrial premature contraction to form a circumferential lesion.

Figures 3, 4:
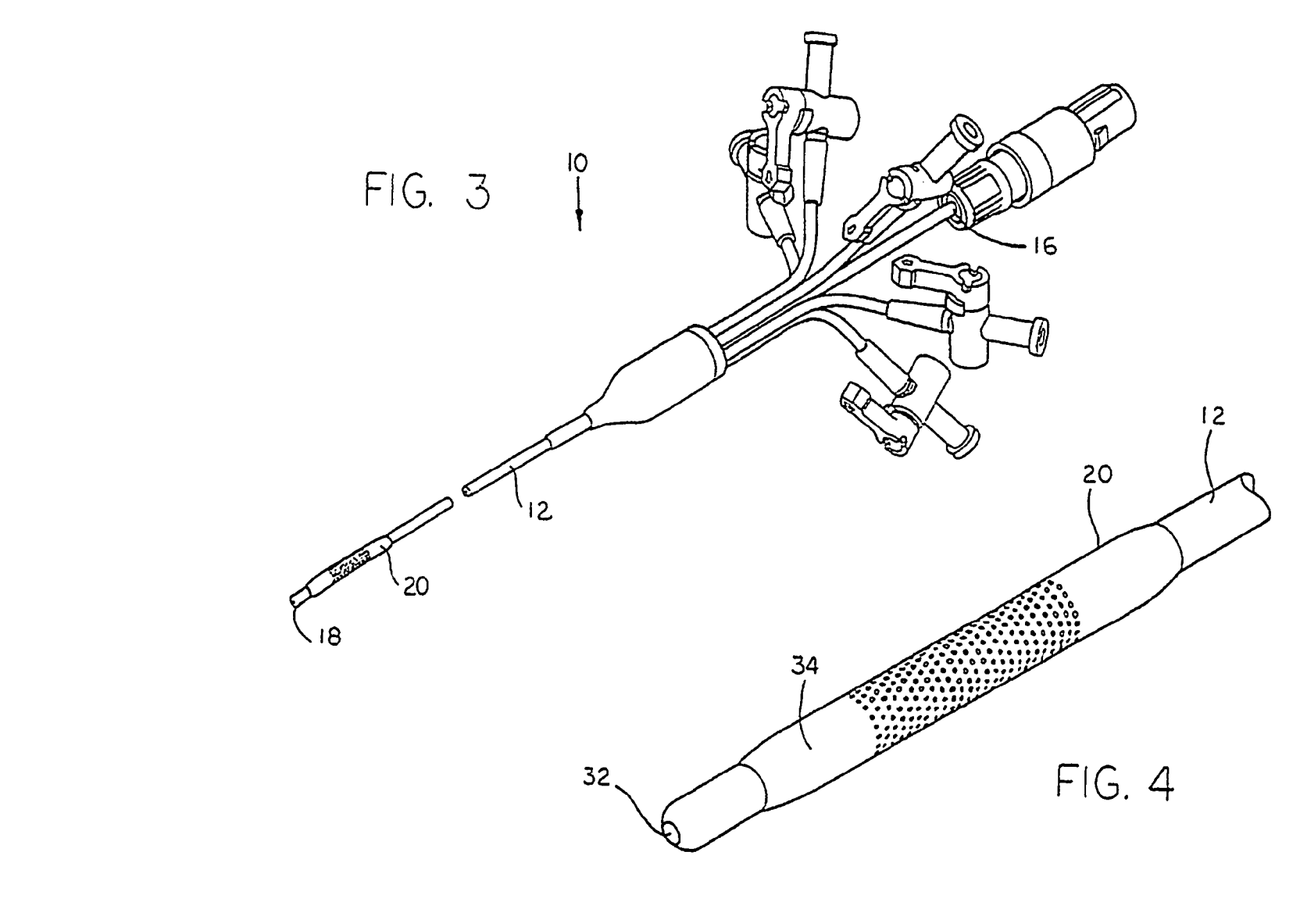
FIG. 3 is a perspective view of the ablation catheter of the present invention with the balloons not inflated.
FIG. 4 is a perspective view of a distal portion of the ablation catheter of FIG. 3 with the balloons not inflated.
Figure 5:
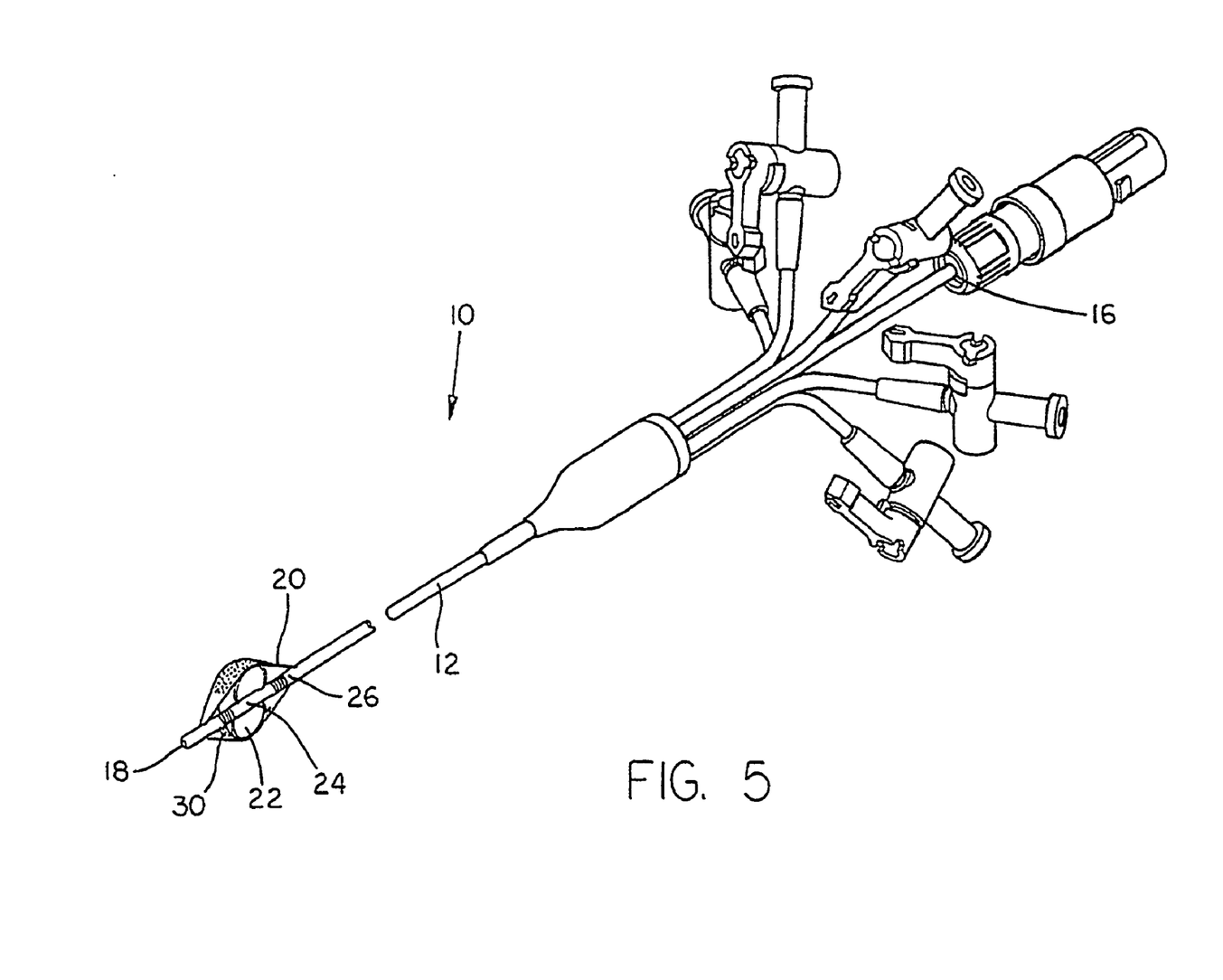
FIG. 5 is a cut away, perspective view of the ablation catheter of FIG. 3 with the balloons inflated.

In a first preferred embodiment the medical device 10 includes the catheter 12 onto which the first balloon 20 and the second balloon 22 are secured as shown in FIGS. 2-9. The catheter 12 of the first embodiment of the present invention contains a proximal end 16 and a distal end 18 as shown in FIGS. 3 and 5. The composition of the catheter 12 is conventional and should be sufficiently pliable to permit the catheter 12 to be advanced through the vasculature into the heart, across the chambers of the heart and ultimately into the pulmonary vein 14. While the distal portion of the catheter 12 may be more pliable than the remaining portion of the catheter 12, the pliability of the catheter 12 may also be consistent throughout the length of the catheter 12. An increase in pliability can be achieved through conventional procedures well known in the industry. To assist in the advancement of the catheter 12 through the vasculature and through the chambers of the heart, the main portion of the catheter 12 may be stiffer and less pliable than the distal portion of the catheter 12. In one embodiment, this main portion can be formed of any conventional catheter material having shape memory or permitting distortion from and subsequent substantial return to its desired shape. This main portion may also be reinforced, for example, by use of a reinforcing braid or other such suitable strand material having high temporal strength. The enhanced pliability of the distal portion of the catheter can be achieved by a number of methods well known in the industry, including the use of a fused flexible tip catheter or a soft tipped catheter comprised of the same or similar materials with similar performance characteristics as are present in the reinforced portion of the catheter 12. In addition, a more pliable distal portion of the catheter 12 can be created through modifications made in the catheter 12 such as by additional drawing of the catheter body to reduce the thickness of the walls, thus achieving enhanced pliability.

The overall length of the catheter 12 should be about 50 to about 150 cm. (20 to about 60 in.).

Figure 6:
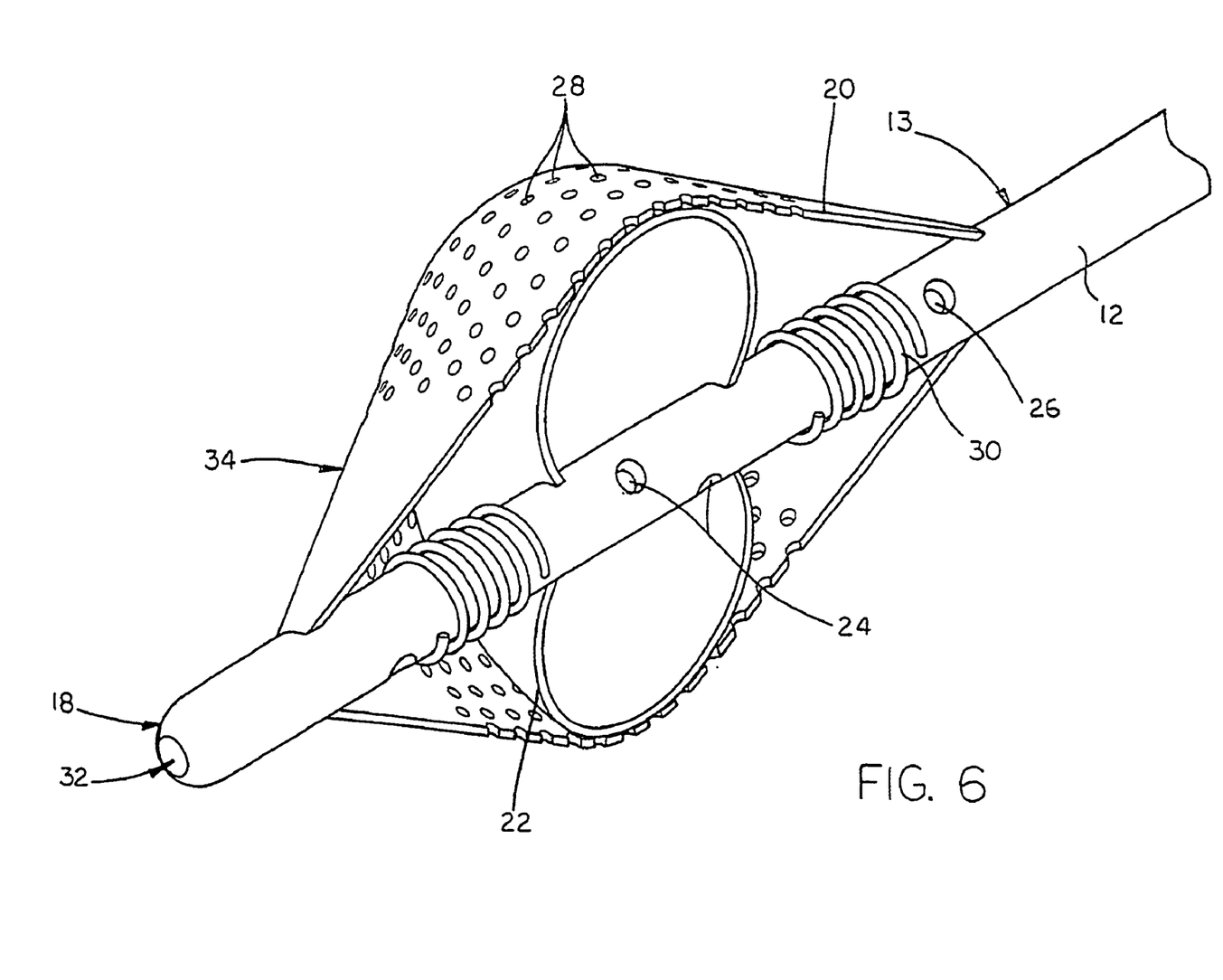
FIG. 6 is a cutaway, perspective view of a distal portion of the ablation catheter of FIG. 5 with the balloons inflated.
Figure 7:
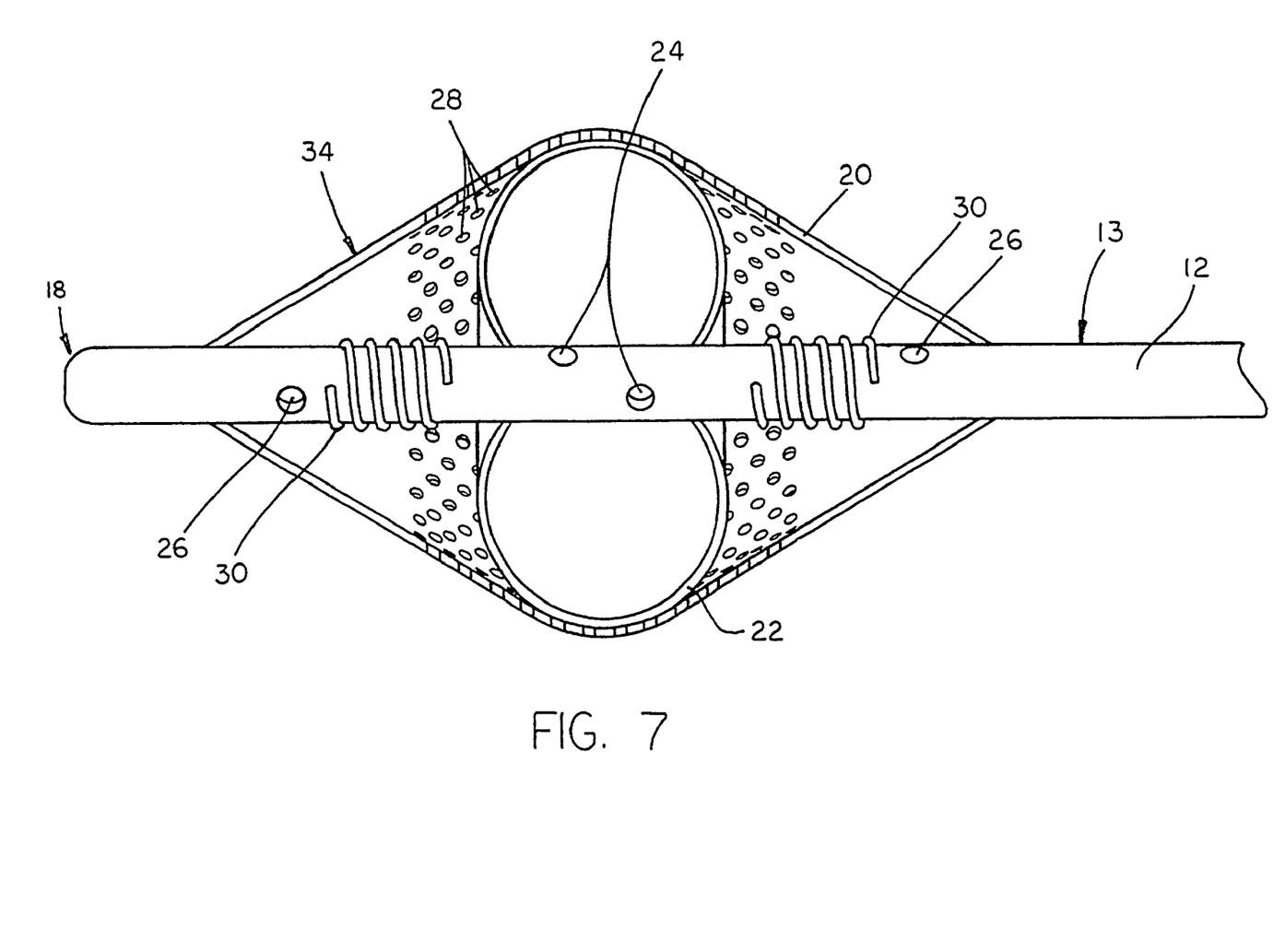
FIG. 7 is a cutaway side view of the distal portion of the ablation catheter of FIG. 5 with the balloons inflated.

The catheter 12 preferably also contains a plurality of conventional lumens which extend from the proximal end 16 of the catheter to or near the distal end 18 of the catheter 12. In one preferred embodiment, the catheter 12 includes at least four separate lumens. The first lumen extends from the proximal end 16 to the distal end 18 of the catheter 12 and ends in a distal opening 32 in the distal end 18 of the catheter 12. This lumen is designed to accommodate a guidewire that passes through the catheter 12 during introduction of the catheter 12 into the pulmonary vein 14. This lumen may also be used for the introduction of a contrast media into the pulmonary vein 14 at a location distal from the balloons 20, 22 of the catheter 12 during the ablation procedure. A second lumen in the catheter 12 receives electrode conductor wires which pass from the proximal end 16 of the catheter to an electrode 30 or electrodes located near the distal end 18 of the catheter 12. The third lumen is designed for introduction of a conductive media into the second, inner balloon 22. This media is utilized to inflate the second, inner balloon 22. For the introduction of media at this location, openings 24 are provided in the catheter 12 at a location within the second, inner balloon 22 as shown in FIGS. 6 and 7. The fourth lumen is designed for the introduction of a conductive media, preferably a saline solution, into the first, outer balloon 20. Media introduction openings 26 are provided in the catheter 12, preferably both proximal and distal from the second inner balloon 22, but inside the first balloon 20 as shown in FIGS. 6 and 7 to receive this conductive media. This conductive media is designed to conduct energy from the electrodes 30 secured to the catheter 12 through the balloon openings 28 in the surface 34 of the outer balloon 22 to contact the inner surface of the pulmonary veins 14. Additional lumens may be provided in the catheter 12 for other conventional utilizations.

The invention also includes an introducing system to introduce conductive media into the space within the first, outer balloon 20, and an ablating system secured to the outside surface 13 of the catheter 12 at a location within the first balloon 20, but outside of the second balloon 22. Other components may also be secured to the catheter 12 to assist in the formation of circumferential ablation lesions, including, for example sensors (not shown) to sense the presence of premature atrial contractions, temperature sensors (not shown) to sense the temperature of the tissue being ablated, markers (not shown) to mark the location of the catheter 12 and its components within the pulmonary vein 14 and other conventional components normally utilized with an ablation catheter 12.

The two balloons 20, 22 are secured to the outer surface 13 of the catheter 12 as shown in FIGS. 3-8. The first, outer balloon 20 typically measures from about 10 mm (0.4 in.) to about 100 mm (4.0 in.) in length and when inflated generally conforms to an ellipsoid shape as shown in FIGS. 5, 6 and 7. The maximum diameter of the first, outer balloon 20 when fully inflated is variable up to about 60 mm (2.4 in.). The second, inner balloon 22 is also secured to the outer surface 13 of the catheter 12 at a location within the first, outer balloon 20 as shown in FIGS. 5, 6 and 7. When inflated, the second, inner balloon 22 measures approximately 2 mm (0.1 in.) to about 100 mm (4.0 in.) in length, preferably 5 mm (0.2 in.) to about 20 mm (0.8 in.), with approximately the same diameter as the first outer balloon 20. Preferably, 23 inflation of the second, inner balloon 22 also inflates the first, outer balloon 20 and maintains the outer balloon 20 in that inflated position throughout the ablation procedure as shown in FIGS. 5, 6 and 7.

The balloons 20, 22 are manufactured according to conventional technology from materials such as a flexible or thermoplastic rubber, urethane, latex, cellulose or other conventional materials and are secured to the catheter 12 conventionally.

Inflation of the balloons 20, 22 is accomplished using conventional methods, preferably using a radiopaque contrast solution, and more preferably a marked saline solution. In addition, if desired, radiopaque marker bands (not shown) may be secured to the surface 34 of the first, outer balloon 20 to mark its relative position in the pulmonary vein 14. Once the proper location in the pulmonary vein 14, or the os of the pulmonary vein, is determined, the catheter 12 may be withdrawn slightly from that location so that the subsequently formed circumferential ablation lesion will be located proximal from the source of the premature atrial contraction.

The balloons 20, 22 when properly inflated should prevent completely the flow of blood through the pulmonary vein 14 around the balloons 20, 22. The balloons 20, 22 are preferably inflated by introduction of media through openings 24 within second, inner balloon 22 which inflates both the inner balloon 22 and the outer balloon 20. Alternatively, or additionally, additional media may be introduced through the media introduction openings 26 in the catheter 12 inside the outer balloon 20 to assist in its inflation. In order to assure that the balloons 20, 22 form a tight seal in the pulmonary vein 14, a contrast media may be injected through the distal opening 32 located in the distal tip 18 of the catheter 12. If any leaks are discovered, additional media may be introduced into the inner balloon 22 until the balloons 20, 22 completely stop the flow of blood in the pulmonary vein 14.

Once the balloons 20, 22 are properly inflated, conductive media is introduced into the outer balloon 22 through the media introduction openings 26 in the outer surface 13 of the catheter 12 located proximal and distal from the second, inner balloon 22. Preferably, two such media introduction openings 26 are provided in the catheter 12, both proximal and distal from the second, inner balloon 22 as shown in FIGS. 6 and 7. In one embodiment, the conductive media is a saline solution marked with markers so that it can be monitored by fluoroscopy, although any appropriate conductive media may be used.

Balloon openings 28 are provided in the surface 34 of the first, outer balloon 20 as shown, for example, in FIGS. 6 and 7. In a preferred embodiment, these balloon openings 28 are formed in a series of lines passing around the surface 34 of the first, outer balloon 20. These balloon openings 28 may be formed in a single line, or in a preferred embodiment, they form two or more lines, each running completely around the surface 34 of the first, outer balloon 20 as shown in FIGS. 6 and 7.

Figure 8:
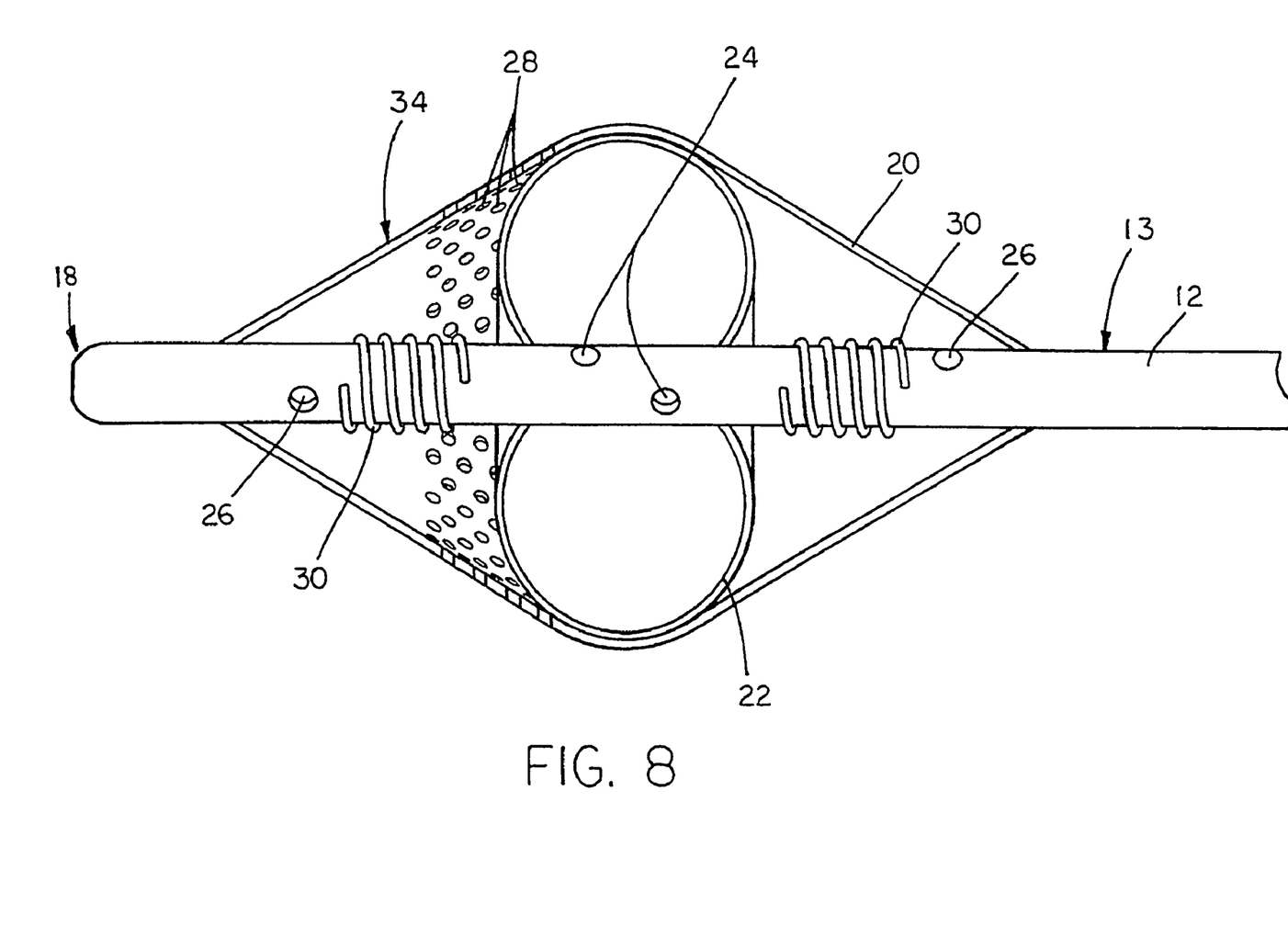
FIG. 8 is a cutaway, side view of the distal portion of the ablation catheter with the balloons inflated, showing an alternative embodiment for the location of the balloon openings in the first, outer balloon.

In an alternative embodiment, these lines of balloon openings 28 are located only distal from the second inner balloon 22 in the first outer balloon 20 as shown in FIG. 8. This alternative structure permits the conductive media to be concentrated distal from the inner balloon 22 within the pulmonary vein 14 against the surface of the tissue and not be dissipated into the left atrium 11.

The electrodes 30, located within the first, outer balloon 20, but outside of the second inner balloon 22, preferably emit radiofrequency energy, which is conducted by the conductive media through the balloon openings 28 in the surface 34 of the first outer balloon 20 to the tissue within the pulmonary vein 14. Because these balloon openings 28 are formed in a line or lines around the surface 34 of the first, outer balloon 20, the conductive energy emitted by the electrodes 30 forms a circumferential lesion inside the pulmonary vein 14.

While the preferred source for the ablation energy is radiofrequency energy, other sources of energy may be utilized, such as microwave, ultrasound or heat. During the ablation process, the energy from the catheter 12 is conducted by the conductive media to the tissue within the pulmonary vein 14. In a preferred embodiment, the impedance of the conductive media should be less than the impedance of the human tissue so that the tissue will heat up to an ablation temperature at a faster rate than does the media.

Figure 9:
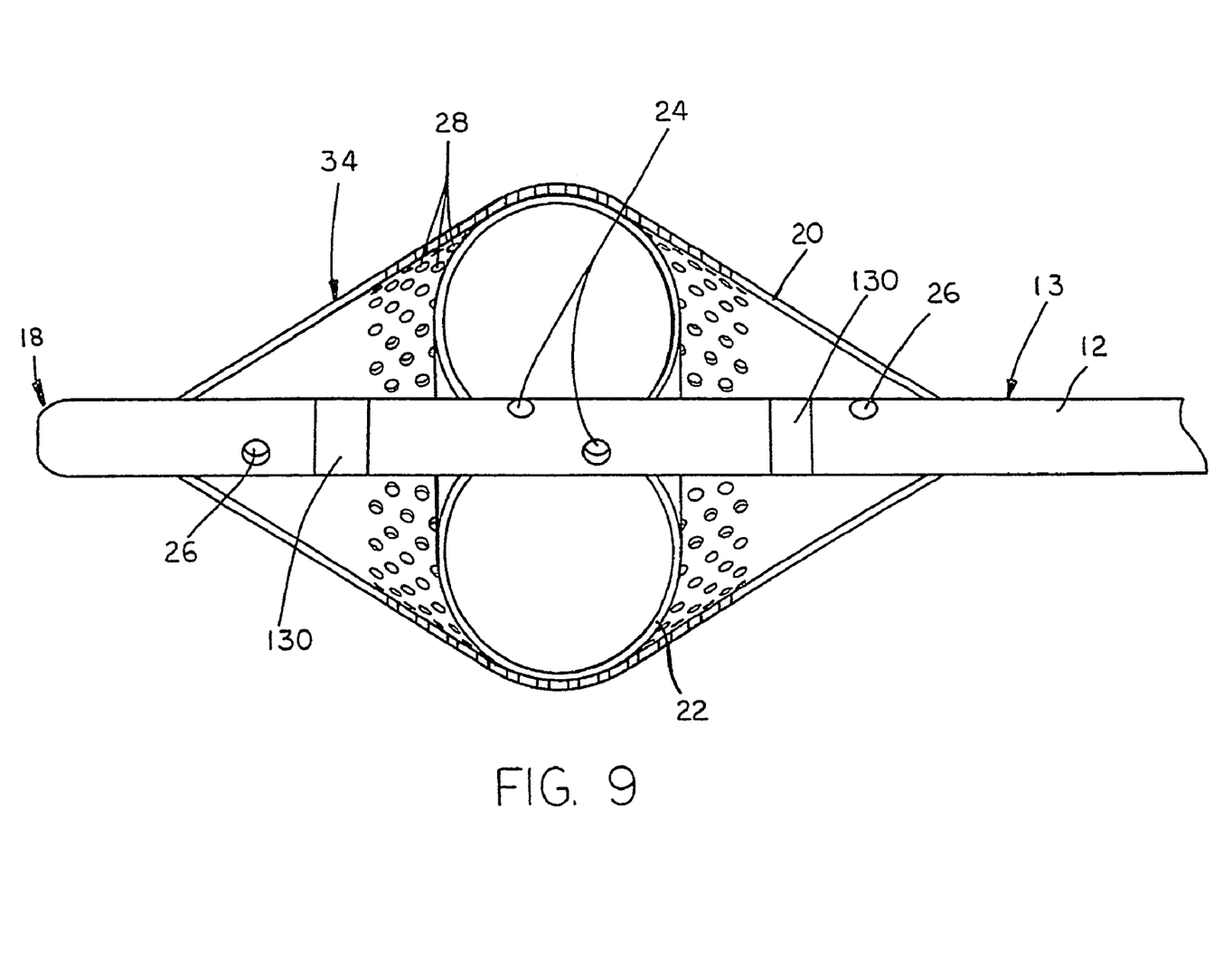
FIG. 9 is a cutaway, perspective view of an alternative embodiment of the ablation catheter of FIG. 7, wherein a ring electrode replaces the coil electrode.
Figure 10:
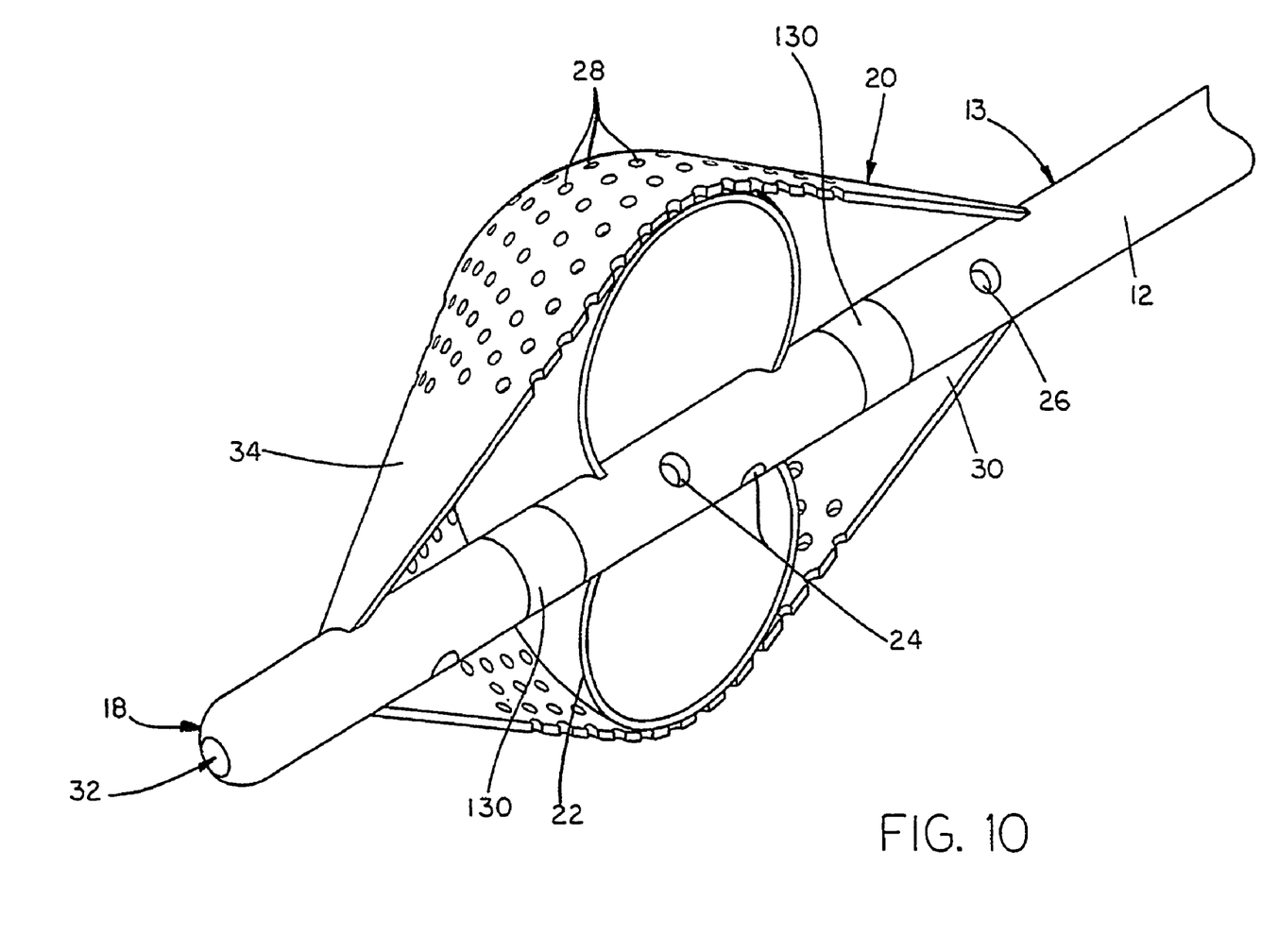
FIG. 10 is a cutaway, side view of the distal portion of the alternative embodiment of the ablation catheter of FIG. 9.

The ablating system can consist of a pair of coil electrodes 30 as shown in FIGS. 6 and 7 or, alternatively, ring electrodes 130 as shown in FIGS. 9 and 10. In a preferred embodiment two electrodes, either coil 30 or ring 130, are secured to the catheter 12, one proximal and one distal from the inner balloon 22, but both inside the outer balloon 20.

In order to monitor the formation of the ablation lesion, a temperature sensor (not shown), such as a thermistor or thermocouple can also be secured to the outer surface 13 of the catheter 12. Sensing electrodes (not shown) can also be secured to the catheter 12 at any appropriate location to monitor electrical activity in the pulmonary vein.

In operation, a modified Seldinger technique is normally used for the insertion of the medical device 10 into the body. Using this procedure, a small skin incision is made at the appropriate location to facilitate catheter or dilator passage. Subcutaneous tissue is then dissected, followed by a puncture of the vessel with an appropriate needle with a stylet positioned at a relatively shallow angle. The needle is then partially withdrawn and reinserted at a slightly different angle into the vessel making sure that the needle remains within the vessel. The soft flexible tip of an appropriate size guidewire is then inserted through, and a short distance beyond, the needle into the vessel. Firmly holding the guidewire in place, the needle is removed, leaving a portion of the guidewire exposed outside of the vessel. The guidewire is then advanced into the right femoral vein and through the inferior vena cava into the right atrium. (The preferred procedure uses the inferior approach to the right and left atria. Procedures for the retrograde and superior approach to the left atrium can also be used and are within the scope of the invention.) With the guidewire in place, a dilator is then passed over the guidewire with an introducer. The dilator and introducer generally form an assembly to be advanced together along the guidewire into the inferior vena cava. The introducer may be a conventional straight introducer or, preferably, a precurved introducer, such as the SL2 introducer sold by Daig Corporation.

A Brockenbrough needle or trocar is then inserted through the lumen of the dilator to the right atrium to be used to create an opening through the interatrial septum, preferably at the fossa ovalis. The entire assembly (dilator, introducer and Brockenbrough needle) passes through the vena cava into the right atrium so that the tip rests against the interatrial septum at the level of the fossa ovalis. The Brockenbrough needle is then advanced through the fossa ovalis after the opening is made through the interatrial septum, the Brockenbrough needle is exchanged for a guidewire. The dilator, guidewire and guiding introducer for the left atrium are then advanced into the left atrium. The dilator is then removed leaving the introducer and guidewire in place in the left atrium. The ablation catheter 12 is then advanced through the lumen of the introducer over the guidewire and into the left atrium. The guidewire is then maneuvered until it enters the appropriate pulmonary vein 14. The catheter 12 is then advanced over the guidewire into the pulmonary vein and the guidewire is removed.

Once the distal end 16 of the ablation catheter 12 has been advanced into the pulmonary vein 14, it may be positioned by use of a sensing electrode (not shown) secured at or near the distal end 16 of the catheter 12. This sensing tip electrode senses electrical activity within the pulmonary vein 14, including atria, premature contractions once the source of the atrial premature contractions has been confirmed to be distal to the inner balloon 22 and outer balloon 20, the inner balloon 22 is inflated by introducing media through the media introduction openings 26 in the catheter 12. By inflating the inner balloon 22, the outer balloon 20 is also inflated. This inner balloon 22 and outer balloon 20 must be sufficiently inflated to prevent completely the flow of blood through the pulmonary vein 14 around the balloons 20, 22. To assure that no blood flows around the balloons 20, 22, marked media may be injected into the pulmonary vein 14 at a point distal from the balloons 20, 22, for example, through the opening 32 in the distal tip 18 of the catheter 12. Any leakage around the balloons 20, 22 can then be determined by fluoroscopy and eliminated by additional pressure on the inside of the inner balloon 22.

The ablating system, preferably a pair of RF coil electrodes 30, or ring electrodes 130, which are secured to the outer surface 13 of the catheter 12 at a location within the outer balloon 20 and outside of the inflated inner balloon 22, then emit energy which is conducted by the conductive media through the balloon openings 28 in the surface 34 of the outer balloon 20 to the surface of the tissue in the pulmonary vein 14. Sufficient energy is emitted to create a circumferential lesion of sufficient width and depth to block completely the passage of the atrial premature contractions through the pulmonary vein 14. The temperature of the tissue of the pulmonary vein 14 may be monitored by temperature sensors, such as thermistors or thermocouples (not shown), located on the surface 13 of the catheter 12 outside the balloons 20, 22. In addition, sensing electrodes (not shown) may be located proximal from the balloons 20, 22 to sense electrical activity through the vessel after the ablation procedure has been completed to assure complete blockage of the pulmonary vein 14. The tissue to be ablated may be at any location within the pulmonary vein 14 or in the os of the pulmonary vein 14.

After the ablation procedure has been completed and tested by use of sensing electrodes, each of the elements of the system are removed from the pulmonary vein 14 and left atrium 11. If desired, additional sensing devices can be introduced into the left atrium 11 to determine whether there are any other sources for the atrial premature contractions in other pulmonary veins 14.

Although embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A medical device for ablation of tissue associated with a vessel connected to the human heart comprising:
    a catheter with a proximal section and a distal section,
    a first balloon with a proximal end and a distal end, the balloon's proximal end being secured to the catheter in the catheter's distal section; the balloon capable of at least partially restricting the flow of blood within the vessel at a location associated with the vessel,
    a second balloon located at least partially within the first balloon, with a proximal end and a distal end, the second balloon's proximal end being secured to the catheter at a location distal to the proximal end of the first balloon,
    an introduction system operating in conjunction with the catheter to introduce a media inside one of the first or second balloons,
    an ablating element secured to the catheter which, in cooperation with the first or second balloon and the media is configured to provide a circumferential ablation to the tissue associated with the vessel.

2. The medical device of claim 1 wherein the ablating element comprises a ring electrode.

3. The medical device of claim 1 wherein the ablating element is secured to the catheter at a location within the first balloon.

4. The medical device of claim 1 wherein the ablating element emits radiofrequency energy.

5. The medical device of claim 1 wherein the ablating element emits ultrasound energy.

6. The medical device of claim 1 wherein the media is a fluid.

7. The medical device of claim 1 wherein the media is conductive.

8. The medical device of claim 7 wherein the conductive media conducts the ablating energy from the medical device through the first balloon toward the targeted tissue to form a circumferential ablation lesion.

9. The medical device of claim 1 wherein the introduction system includes a lumen extending from a proximal end of the catheter to the distal section of the catheter, and includes an opening into the first balloon.

10. The medical device of claim 9 wherein the introduction system includes a second lumen extending from a proximal end of the catheter to the distal section of the catheter, and includes an opening into the second balloon.

11. The medical device of claim 1 wherein the vessel is a pulmonary vein.

12. The medical device of claim 1 wherein the medical device is adapted to create a circumferential transmural lesion in the ostium of the pulmonary vein.

13. A medical device for ablation of tissue associated with a pulmonary vein comprising:
    a catheter with a proximal section and a distal section,
    a first balloon with a proximal end and a distal end, the balloon's proximal end being secured to the catheter in the catheter's distal section; the balloon capable of at least partially restricting the flow of blood within the vein at a location associated with the vein, a second, balloon with a proximal end and a distal end, the balloon's proximal end being secured to the catheter at a location distal to the proximal end of the first balloon, a first lumen operating in conjunction with the catheter to introduce a media inside the first balloon, a second lumen operating in conjunction with the catheter to introduce a media inside the second balloon, wherein the ablating element emits radiofrequency energy or ultrasound energy, and wherein the medical device is adapted to create a circumferential transmural lesion in the ostium of the pulmonary vein.

14. A process for ablation of tissue associated with a vessel of a human heart comprising:

introducing a medical device to a position adjacent to tissue associated with the vessel, wherein the medical device comprises an extended catheter, a first balloon with a proximal end and a distal end, the first balloon's proximal end being secured to the catheter in the catheter's distal section, a second balloon with a proximal end, the second balloon's proximal end being secured to the catheter at a location distal to the proximal end of the first balloon, at least partially sealing the vessel to restrict at least partially the flow of blood through the vessel, passing a conductive media through a lumen in the catheter to the first balloon, conducting energy from an electrode secured to the catheter by use of the conductive media through the first balloon to the tissue, forming a circumferential ablation in the tissue.

15. The process of claim 14 wherein the energy is radiofrequency energy.

16. The process of claim 14 wherein the energy is ultrasound energy.

17. The process of claim 14 wherein the tissue is a pulmonary vein.

18. The process of claim 17 further comprising a step of positioning the medical device proximal the located source of an atrial premature contraction.

19. The process of claim 18 further comprising a step of sensing electrical activity within the pulmonary vein.

20. The process of claim 19 further comprising a step of locating a source of an atrial premature contraction within the pulmonary vein using the sensed electrical activity.

* * * * *